(12) United States Patent
Petit et al.

(10) Patent No.: US 8,419,744 B2
(45) Date of Patent: Apr. 16, 2013

(54) DEVICE FOR ESTABLISHING AN ANATOMICAL REFERENCE POINT OF AN INTERVERTEBRAL DISC

(75) Inventors: Dominique Petit, Verton (FR); Thomas Droulout, Poissy (FR); Max Aebi, Bienne (CH)

(73) Assignee: Spinevision SA, Anthony Cedex (FR)

( * ) Notice: Subject to any disclaimer, the term of this patent is extended or adjusted under 35 U.S.C. 154(b) by 0 days.

(21) Appl. No.: 13/295,425

(22) Filed: Nov. 14, 2011

(65) Prior Publication Data

US 2012/0116517 A1  May 10, 2012

Related U.S. Application Data

(63) Continuation of application No. 12/997,840, filed as application No. PCT/FR2009/000704 on Jun. 12, 2009.

(30) Foreign Application Priority Data

Jun. 13, 2008  (FR) ...................................... 08 03314

(51) Int. Cl.
*A61F 2/46* (2006.01)
(52) U.S. Cl.
USPC ........................................ 606/99; 623/17.11
(58) Field of Classification Search .... 623/17.11–17.16; 606/130, 99, 86 A
See application file for complete search history.

(56) References Cited

U.S. PATENT DOCUMENTS

| 7,632,282 | B2 | 12/2009 | Dinville | |
|---|---|---|---|---|
| 8,092,495 | B2* | 1/2012 | Boulis et al. | 606/246 |
| 2005/0234449 | A1* | 10/2005 | Aferzon | 606/61 |
| 2005/0273167 | A1* | 12/2005 | Triplett et al. | 623/17.11 |
| 2006/0084986 | A1 | 4/2006 | Grinberg et al. | |
| 2006/0149273 | A1 | 7/2006 | Ross et al. | |
| 2006/0149278 | A1* | 7/2006 | Abdou | 606/90 |
| 2007/0083210 | A1* | 4/2007 | Hestad et al. | 606/86 |
| 2009/0216239 | A1* | 8/2009 | Johansson et al. | 606/99 |
| 2010/0023018 | A1* | 1/2010 | Theofilos | 606/96 |

FOREIGN PATENT DOCUMENTS

| CH | 692023 A5 | 1/2002 |
|---|---|---|
| DE | 29703947 U1 | 6/1997 |
| FR | 2887762 A | 1/2007 |

OTHER PUBLICATIONS

Written Opinion of the International Searching Authority dated Dec. 14, 2010.
International Search Report dated Oct. 30, 2009.

* cited by examiner

*Primary Examiner* — Eduardo C Robert
*Assistant Examiner* — Lynnsy Schneider
(74) *Attorney, Agent, or Firm* — Bachman & LaPointe, P.C.

(57) ABSTRACT

The disclosure relates to a device for establishing an anatomical reference point of an intervertebral disc for the attachment of at least one instrument Intended for the implantation, through a posterior or posterolateral approach, of a disc prosthesis or osteosynthesis cage as a replacement for the intervertebral disc. The device includes at least two means for bone anchorage each intended to be attached to a vertebra adjacent to the disc, a coupling element for the instrument and elements for adjusting the position of the coupling element relative to the position of the disc.

13 Claims, 5 Drawing Sheets

DEVICE FOR ESTABLISHING AN ANATOMICAL REFERENCE POINT OF AN INTERVERTEBRAL DISC

CROSS-REFERENCE TO RELATED APPLICATIONS

This application is a continuation of co-pending U.S. application Ser. No. 12/997,840, filed Jul. 12, 2011, which is a National Phase Entry of International Application No. PCT/FR2009/000704, filed on Jun. 12, 2009, which claims priority to French application Ser. No. 08/03314, all of which are incorporated by reference herein.

BACKGROUND AND SUMMARY

The invention relates to a device for establishing an anatomical reference point for an intervertebral disc to be replaced by a disc prosthesis or an osteosynthesis cage through posterior or posterolateral approach. The device according to the invention is more particularly, but not exclusively, intended for establishing the anatomical reference point of at least one disc positioned between the lumbar vertebrae L3 and the sacral vertebra S1.

Conventionally, the intervertebral disc is removed and the disc prosthesis is positioned through an anterior or lateral approach of the disc and more rarely through a posterior approach. The side of the approach selected to execute the surgical gesture depends on the gesture to be executed, the surgeon's preference and/or the patient's anatomical constraints.

The anterior and lateral approaches, however, have the drawback of being relatively invasive. They also imply a surgical gesture which is delicate as regards the associated risks and difficult as regards technique. The stage L5-S1 is particularly delicate because it requires pushing the aortas aside and so a bad estimation by the surgeon and an error in the gesture could involve vascular complications. Other complications may further occur, such as post-operative pains which may require removing the positioned prosthesis and/or total osteosynthesis from the instrumented level.

The posterior approach involves fewer risks of complications and is further less invasive. The drawback of such an approach however lies in that the vision of the operative field is extremely reduced. Then, in order to enable the surgeon to visually accede the operative field, it is often necessary to remove bone materials.

The invention aims at remedying the problems of approaching the intervertebral disc by providing a device for establishing an anatomical reference point of the disc to be replaced prior to the implantation, through the posterior or posterolateral approach, of an implant such as a disc prosthesis or osteosynthesis cage, and thus to be able to proceed, during the implantation, according to a little invasive approach of the disc to be replaced, while ensuring a precise and aligned implantation of the disc implant as a replacement for the removed disc. For this purpose and according to a first aspect, the invention provides a device for establishing an anatomical reference point of an intervertebral disc for the attachment of at least one instrument intended for the implementation, through a posterior or posterolateral approach of an implant, such as a prosthesis disc or an osteosynthesis cage as a replacement for the intervertebral disc. The device comprises first and second means for bone anchorage each intended to be fixed on an a vertebra adjacent to the intervertebral disc, a coupling element whereon the instrument is intended to be attached, the coupling element being mounted between the first and the second means for bone anchorage and means for adjusting the position of the coupling element relative to the position of the intervertebral disc.

Advantageously, the adjusting elements comprise a first and a second element for establishing a reference point of the intervertebral disc to be replaced, the first element composing a reference point relative to the spinous processes of the vertebra surrounding the intervertebral disc to be replaced, and the second element constituting a reference point indicating the direction of the intervertebral disc to be replaced, with the second element being mounted to move on the first element. More particularly, according to a particular configuration, the adjusting elements comprise a platform having a longitudinal axis BB provided with an element for viewing the intervertebral disc having a geometrical axis, the viewing element being mounted to move on a platform so as to orient the geometrical axis towards the intervertebral disc, and means for connecting the platform to the first and the second means for bone anchorage, the connection means being so arranged as to form a ball and socket link.

So, thanks to the motions of the platform with respect to the means for bone anchorage and of the viewing element relative to the platform, an anatomical reference point of the intervertebral disc to be treated is obtained. The platform constitutes a reference point relative to the patient's spine and more particularly relating to the spinous processes crest of the at least two vertebras surrounding the disc to be replaced. The viewing element constitutes a reference point indicating the direction of the intervertebral disc to the replaced. The degrees of freedom of the adjusting elements with respect to each other make it possible to adjust the viewing element with respect to the intervertebral disc and thus to ensure a precise and aligned implantation of the implant in the intervertebral space obtained after the removal of the disc.

Advantageously, the viewing element is arranged with the platform so as to have a degree of freedom in translation along the axis BB. Advantageously, the viewing element is so arranged with the platform as to have a degree of freedom in rotation about an axis perpendicular to the axis CC.

It can also be provided for the adjusting elements to comprise means for adjusting the orientation of the viewing element arranged to enable the pivoting of the viewing element about an axis perpendicular to the axis BB. According to a particular configuration, the adjusting means comprise an intermediate part positioned between the viewing element and the platform, with the intermediate part having a convex face whereon the viewing element is mounted to move, the intermediate part having a degree of freedom in translation along the axis BB.

Advantageously, the coupling element is mounted to slide along the viewing element. It is then possible to adjust the position of the coupling element as a function of the patient's anatomy, the implementation of the elements such as, for example, the depth of insertion of the means for bone anchorage into the vertebra as well as the dimensions of the implantation instrument. Then, it is possible to implement standard implementation instruments.

In order to enable the forming of a "tunnel" with a view to cleaning both sides of the intervertebral space or a bilateral positioning of the implant or implants, the coupling element comprises two coupling points for the respective attachment of an implantation instrument, both coupling points being positioned on either side of the viewing element. It can also be provided to arrange additional coupling means on the platform to enable the attachment of the device on a holding equipment able to be attached on a support, for example on a hinged arm fixed on the table of operation and provided with complementary coupling means. Advantageously, the device comprises a linking bar able to link the first and the second means for bone anchorage together, the adjusting elements and advantageously the platform being mounted on the linking bar. It can also be provided, according to an advantageous configuration, for the adjusting elements and the linking bar to comprise mutual association means, said means being so arranged as to form a ball and socket link.

According to a particular embodiment of the invention, the mutual association means comprise a ball-and-socket joint provided on the linking bar cooperating with a recess having a matching shape arranged on the adjusting elements and advantageously on the platform or reversely. Advantageously, the device comprises first and second means intended to respectively lock, on the one hand, the platform on the first and second means for bone anchorage, and on the other hand, the viewing element on the platform.

The invention also relates to a system enabling the implantation of a disc prosthesis or an osteosynthesis cage through a posterior or posterolateral approach, the system including a device for establishing an anatomical reference point of an intervertebral disc such as previously described and at least an instrument for implanting a disc prosthesis or an osteosynthesis case attached to the device. According to a particular configuration, the implantation instrument comprises a linking arm, one end of which is mounted to be hinged on the coupling element of the device, with the other end of the arm being provided with a tubular portion curved towards the intervertebral disc to be replaced. According to another particular configuration, the implantation instrument comprises a linking arm mounted to be fixed on the coupling element. This linking arm is provided with receiving means intended to receive a tubular portion having a curved or straight shape and so configured as to hold the tubular portion in a position oriented towards the intervertebral disc to be replaced.

BRIEF DESCRIPTION OF THE DRAWINGS

Other objects and advantages of the invention will appear during the following description and while referring to the appended drawings, wherein.

DETAILED DESCRIPTION

Figure 1:
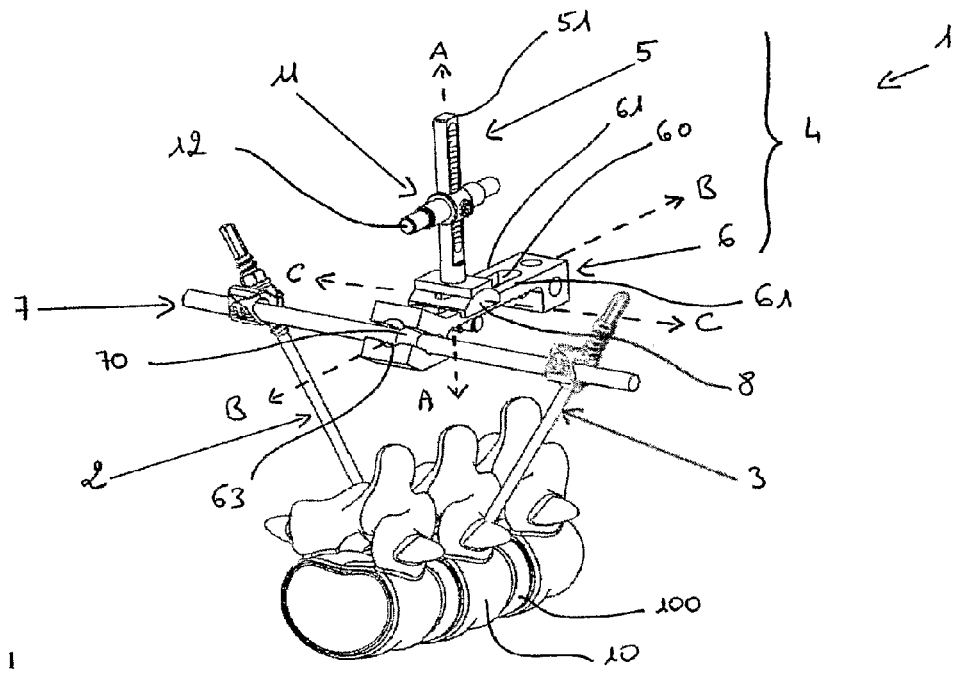
FIG. 1 shows a schematic view of a device for establishing an anatomical reference point of an intervertebral disc to be replaced according to the invention, with the device being fixed on an overlying vertebra.

While referring to FIG. 1, the device 1 is described, which makes it possible to establish an anatomical reference point of an intervertebral disc 100 to be replaced, so as to enable an implantation, through a posterior or posterolateral approach, of a disc prosthesis or an osteosynthesis cage using an adapted implantation instrument. In order to facilitate the understanding of the following discussion, the device 1 for establishing an anatomical reference point of the disc to be replaced will be called "reference point device 1" in the following. The reference point device 1 according to the invention comprises two means for bone anchorage 2, 3 and adjusting elements 4 mounted to be hinged at the proximal ends of the means for bones anchorage 2, 3.

The adjusting elements 4 comprise a platform 6 provided with a viewing element 5 for the intervertebral disc 100 to be replaced, as well as means for connecting the platform with the first and second means for bone anchorage 2, 3, the connection means forming a ball and socket link. As will be seen hereinafter, the platform 6 is intended for positioning the viewing element 5 in alignment with the patient's spine axis and the viewing element for establishing the direction of the intervertebral disc 100 to be replaced. The platform 6 has the shape of a bar with a rectangular cross-section with a longitudinal axis BB, and comprising inside a longitudinal slot 60 limited by two side rails 61. Advantageously, the slot 60 opens onto the upper and lower faces of the bar.

In the described embodiment, the platform 6 is attached on the means for bone anchorage 2, 3 by a linking bar 7 positioned between the means for bone anchorage 2, 3. As will be seen in the following, the linking bar 7 shall have to be positioned horizontally between the means for bone anchorage 2, 3. Advantageously, the platform 6 and the connecting bar 7 comprise mutual association means so arranged as to form a ball and socket link. More particularly, the linking bar 7 comprises a spherical hinge 70 cooperating with a recess having a matching shape arranged at one of the ends 62 of the platform 6. In this embodiment, the mutual association means compose the means for connecting the platform 6 to the first and second anchoring means 2, 3.

It may be advantageous to also provide for a hinged connection of the linking bar 7 with the means for bones anchorage 2, 3. Advantageously, such connection is provided with a three dimensional system such as the connector described in the application for a patent EP 1233710.

When the adjustment of the position of the platform 6 is completed, the platform is locked using a nut or a locking screw inserted into a through hole 63 arranged at the end 62 of the platform 6 and opening into the recess receiving the spherical hinge 70 of the linking bar 7. In order to optimize the stability of the platform, the latter can also be attached to an operative table by means of a hinged arm (not shown). Therefore, the platform advantageously comprises coupling means configured to corporate with complementary coupling means arranged on the hinged arm.

The viewing element 5 is in the shape of a rod 51 positioned in a plan substantially vertical with respect to that of the platform 6. The rod 51 having a geometrical axis AA is mounted to be moved on the platform 6 so as to enable the orientation of the viewing element 5, along the geometrical axis thereof, towards the intervertebral disc 100 to be replaced. More particularly, the viewing element 5 is arranged with the platform 6 to have a degree of freedom in translation according to the axis BB of the platform 6. In the embodiment described, the viewing element 5 is mounted to slide along the side rails 61 of the platform 6.

Advantageously, the viewing element is arranged with the platform 6 to also have a degree of freedom in rotation about an axis CC perpendicular to the axis BB of the platform 6. In the embodiment described, the degree of freedom in rotation is obtained using an intermediate part 8 positioned between the viewing element 5 and the platform 6.

More particularly, the intermediate part 8 has a convex face 80 whereon the viewing element 5 is mounted to move, with the convex face being oriented so as to enable the pivoting of the viewing element 5 towards one or the other of the ends of the alignment platform 6 (pivoting about the axis CC). The intermediate part 8 is mounted to slide along the side rails 61 of the platform 6. The intermediate part 8 described composes the means for adjusting the orientation of the viewing element 5 related to the intervertebral disc 100 to be replaced. Of course, this is an exemplary embodiment and the invention is not limited to such adjusting means. When the position of the viewing element 5 on the platform 6 is adjusted and the orientation thereof related to the intervertebral disc 100 is adjusted, the latter is locked in position using means 66 which form a tightening vice.

Figure 4:
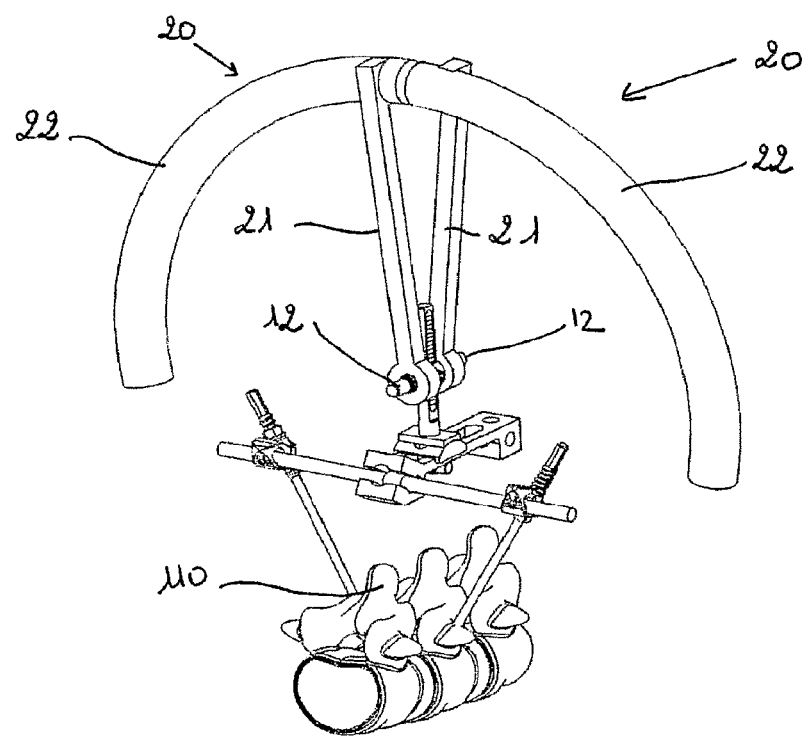
FIG. 4 shows a view of the device of FIG. 2 provided with two instruments for implantation of disc prostheses or osteosynthesis cages.

In order to enable the attachment of an implantation instrument for a disc prosthesis on the reference point device 1, the adjusting elements 4 comprise a coupling element 11 provided with at least one coupling point 12 in the shape of an arm extending parallel to the axis of the platform 6. In the embodiment described, the coupling element 11 has two coupling points 12 positioned opposite each other. Thus, the reference point device 1 can be provided with two implantation instruments, as illustrated in FIG. 4.

In order to enable the implementation of a standard implantation instrument, the coupling element 11 is advantageously mounted to slide along the rod 51 of the viewing element 5. It is thus possible to adjust the height of the coupling point of the implantation instrument relative to the intervertebral disc to be replaced and thus to adjust the position of the coupling point as a function of the patient's anatomy, the implementation of the elements composing the reference point device 1 (such as for example, the depth of insertion of the means for a bone anchorage into the vertebra) as well as the dimensions of the implantation instrument. The locking of the coupling element 11 on the rod 51 is obtained by screwing the latter on the rod 51 of the viewing element 5. For this purpose, it will be advantageous to provide on the rod 51 of the viewing element 5 some notches 52 cooperating with some matching notches on the coupling element 11.

Figure 2:
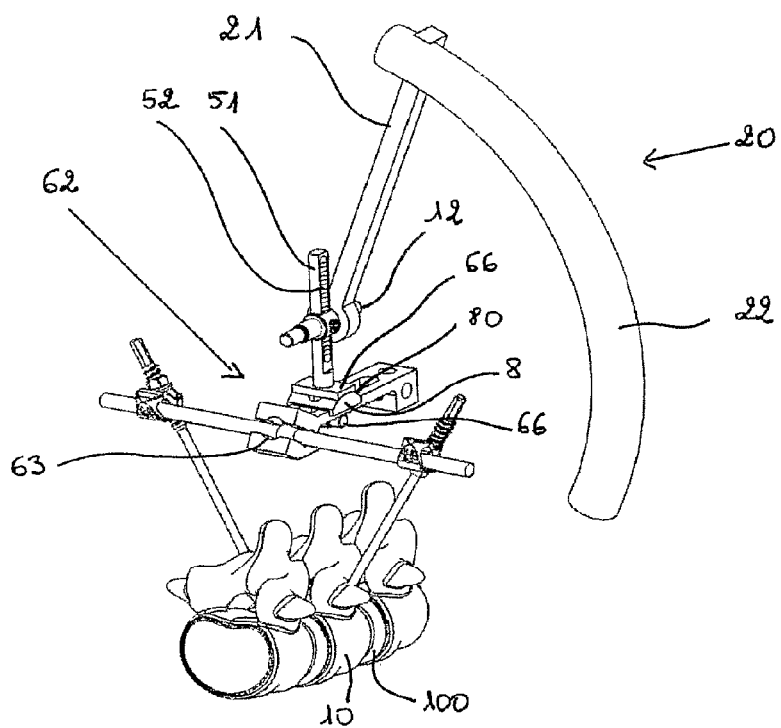
FIG. 2 shows a view of the device of FIG. 1 provided with an instrument for implanting a disc prosthesis or an osteosynthesis cage.
Figure 3:
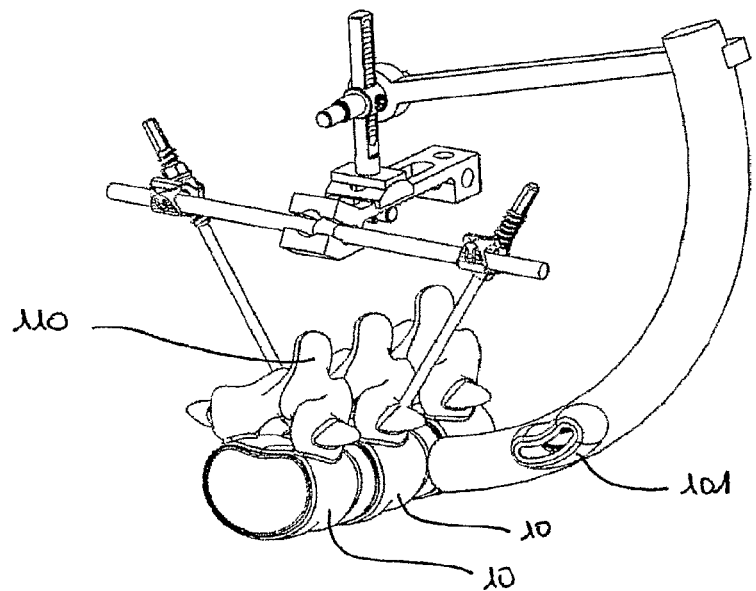
FIG. 3 shows a view of the device of FIG. 2, wherein the implantation instrument is illustrated in the position of implantation of a disc prosthesis or an osteosynthesis cage.

The implantation instrument 20 associated with the reference point device 1 described above comprises a linking arm 21 able to be mounted to be hinged on the coupling point 12 of the coupling element 11 at one of the ends thereof, with the other ends being provided with a tubular portion 22 curved according to a determined radius towards the intervertebral disc 100 to be replaced (FIG. 2). As will be seen hereinafter, the positioning of the coupling point 12 established after an adjustment, and the fit of the elements 4, i.e. the linking bar 7, the platform 6 and the viewing element 5 relative to the intervertebral disc 100 to be replaced, enables the implantation instrument, when moved to the implementation position, to be automatically and accurately positioned in alignment with the plane of the intervertebral disc 100 to be replaced, thus making it possible to remove the intervertebral disc, to clean the intervertebral space and to position the disc prosthesis 101 or the osteosynthesis cage (FIG. 3). It should be noted that the curved portion is so arranged on the linking arm 21 that, when the reference point device 1 is provided with two implantation instruments, the curved portion 22 of each implantation instruments is positioned in the same plane (FIG. 3).

The method for anatomically establishing a reference point for the intervertebral disc 100 to be replaced and establishing the approach using the device 1 for establishing the reference point described above is as follows. The first step consists in anchoring both means for bone anchorage 2, 3 into the vertebra 10. In the embodiment described, the means for bone anchorage 2, 3 are anchored on the same vertebra. It can be independently of the over- or underlying vertebra of the intervertebral disc 100 to be replaced. The linking bar 7 is then attached between the two means for bone anchorage 2, 3.

Figure 5A:
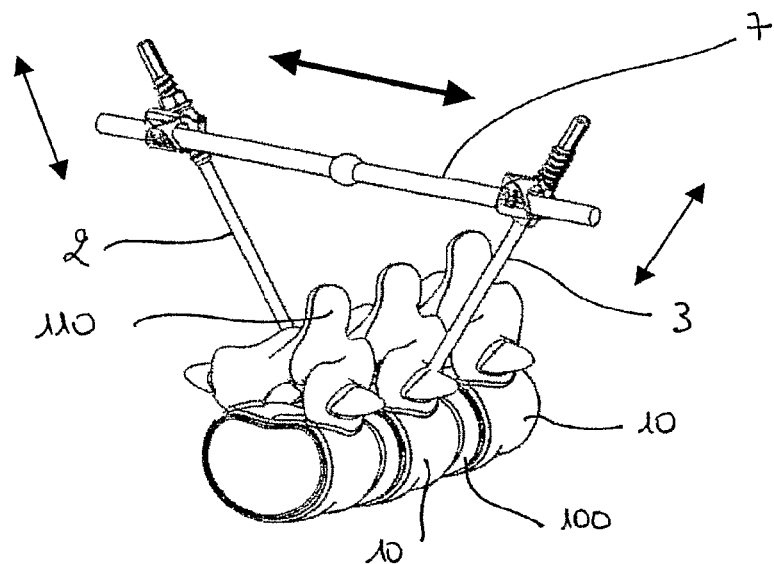
FIGS. 5a to 5d show the steps of positioning the device of FIG. 1.

The following steps are intended to enable the perfect centering of the prosthesis in the intervertebral space obtained when the intervertebral disc has been removed during the implementation of the associated implantation instrument. Firstly, the linking bar 7 is positioned between the two means for bone anchorage 2, 3. The linking bar 7 should be positioned in the horizontal plane and the hinge 70 forming the ball and socket linking of the linking bar 7 should be positioned in alignment with the spinous processes 110 of the vertebrae 10 as shown in FIG. 5a by the two series of arrows. The horizontality of the linking bar 7 shall be checked using a level.

Figure 5B:
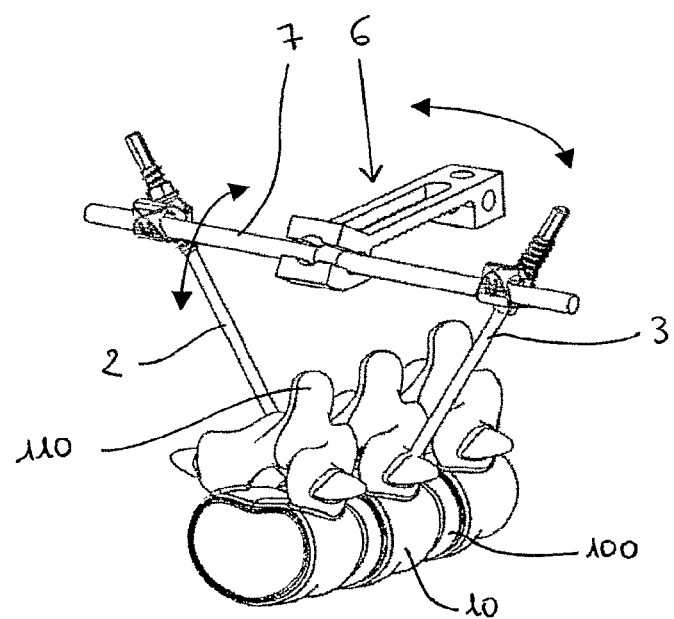

When the horizontality of the linking bar 7 and the alignment of the hinge are checked, the platform 6 mounted on the linking bar 7 at the hinge is adjusted so as to be positioned in a plane substantially perpendicular to the plane of the disc 100 considered, with the position of the platform 6 depending on the patient's lordosis (FIG. 5b). The adjustment is made possible thanks to the existence of the ball and socket link between the linking bar 7 and the platform 6. The position of the alignment platform 6 can be checked using the visible line formed by the spinous processes seen on the patient's back. Once the position of the platform 6 is determined, the latter is then blocked in position using the first locking means.

Figure 5C:
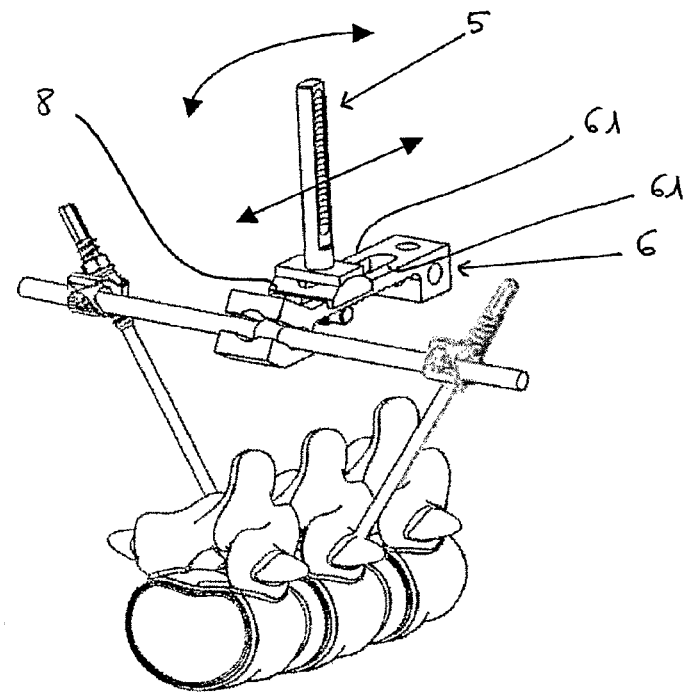
Figure 5D:
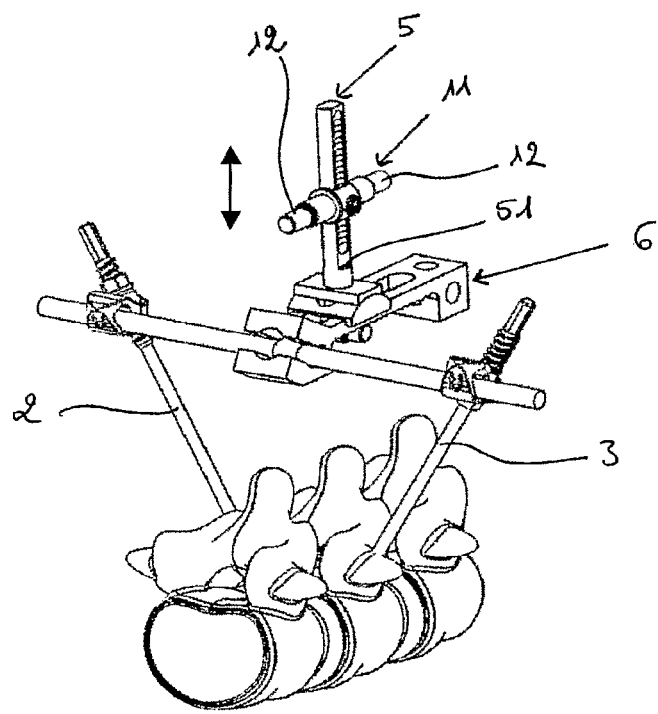

Then, the viewing element 5 is adjusted relative to the intervertebral disc 100 by moving in translation the viewing element along the side rails 61 of the platform 6 and/or pivoting the viewing element 5 on the intermediate part 8, so as to orientate the geometrical axis of the viewing element 5 towards the intervertebral disc 100 to be replaced. The motions of the viewing elements 5 are shown in FIG. 5c by two arrows. The adjustments are checked by means of a side fluoroscopy. Once the position of the viewing element 5 desired is reached, the latter is then locked in position using the second locking means.

And finally, the height of the coupling point 12 of the implantation instrument on the rod 51 of the viewing element 5 is adjusted by sliding the coupling element 11 along the rod 51. Once the required height of the coupling element 11 is reached, the latter is locked on the rod. As mentioned above, the position of the coupling element 11 is checked using a side fluoroscopy. The thus calibrated device 1 for establishing a reference point is ready for receiving the implantation instrument 20.

It should be noted that, in order to clearly show the various adjustments to be carried out during the positioning of the device 1 for establishing a reference point, all the adjusting element 4 have not been shown in FIGS. 4a to 4c. Of course, the adjusting elements 4 are not mounted when and as the associated adjustments are carried out as shown in the above mentioned Figures.

Figure 6:
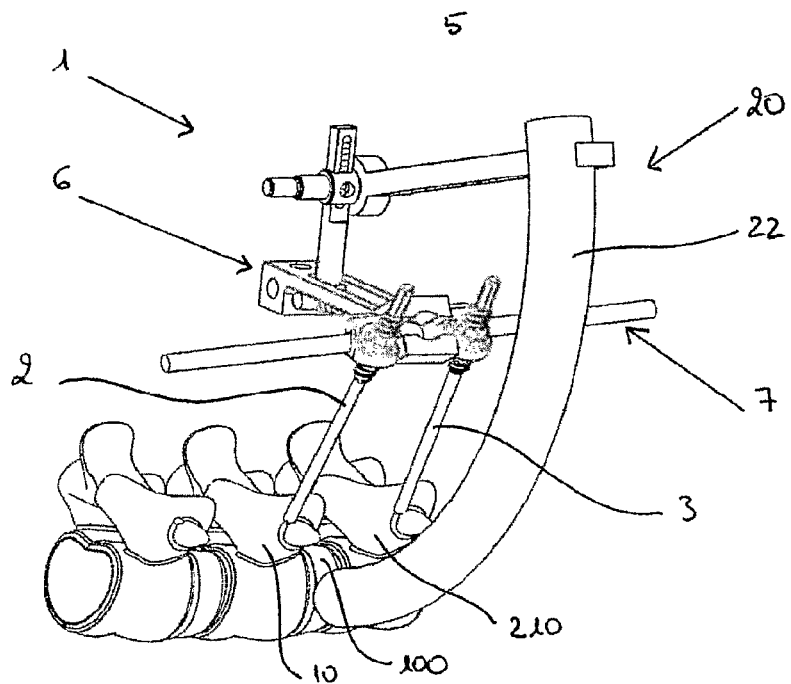
FIG. 6 shows the device of FIG. 1 provided with an implantation instrument, the device being attached to the over- and underlying vertebras.
Figure 7:
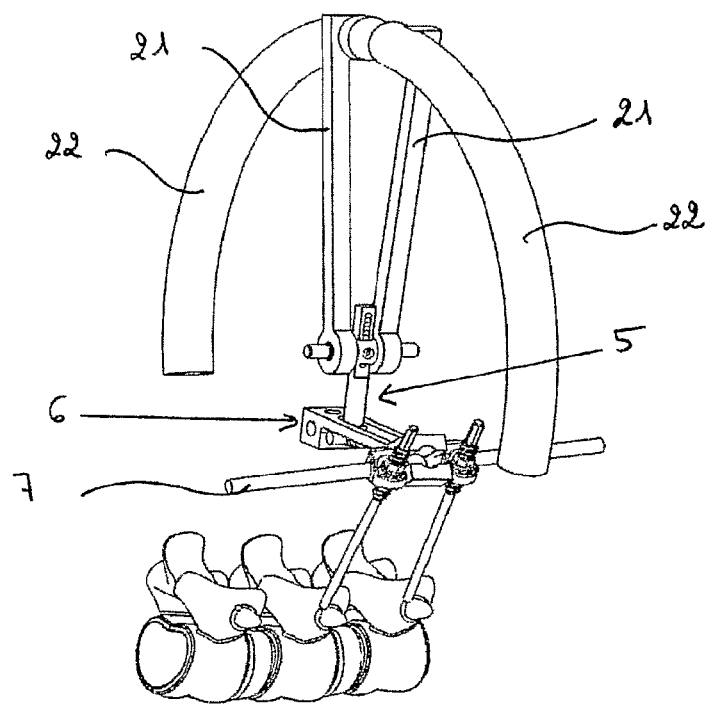
FIG. 7 shows the device of FIG. 6 provided with two implantation instruments.

In the illustrated example, the means for bone anchorage are attached on the same vertebra. Of course the device 1 for establishing a reference point can be anchored on two different vertebrae 10, 210 positioned on either side of the intervertebral disc 100 to be replaced, as illustrated in FIGS. 6 and 7. The vertebrae intended to receive the means for bone anchorage can be distant from each other leaving at least one intermediate vertebra without any anchoring means. In this configuration, the device 1 for establishing a reference point will also comprise a linking bar 7, the alignment platform 6 being positioned perpendicularly to the axis of the spinous processes and along the axis of the intervertebral disc. The degree of freedom in translation of the viewing element 5 is then provided for positioning the latter along the axis of the spinal crests.

The invention is described above as an example. It should be noted that the persons skilled in the art can make various alternate embodiments of the invention without leaving the scope of the invention.

The invention claimed is:

1. A device for establishing an anatomical reference point of an intervertebral disc for the attachment of at least one instrument intended for the implantation, through a posterior or posterolateral approach, of a disc prosthesis or osteosynthesis cage as a replacement for the intervertebral disc, the device comprising:
   first and second bone anchors each adapted to be attached to a vertebra;
   a coupling element on which the instrument is intended to be attached, the coupling element being mounted between the first and the second bone anchors; and
   elements operably adjusting a position of the coupling element relative to a position of the intervertebral disc;
   the elements operably adjusting a position of the coupling element comprising a horizontal platform having a longitudinal axis provided with an element for viewing the intervertebral disc having a geometrical axis; the viewing element being positioned in a plane substantially vertical along a vertical axis and being mounted to move on the platform so as to orient the geometrical axis in the direction of the intervertebral disc; and a connector operably connecting the platform to the first and second bone anchors, the connector being arranged to form a ball and socket link, the platform rotating relative to the connector around an axis perpendicular to the longitudinal axis and the vertical axis; and
   the viewing element being arranged with the platform so as to have a degree of freedom in translation along the longitudinal axis.

2. A device for establishing an anatomical reference point of an intervertebral disc according to claim 1, wherein the platform is for establishing a reference point relative to the spinous processes of the vertebra surrounding the intervertebral disc to be replaced, the viewing element is for establishing a reference point indicating the direction of the intervertebral disc intended to be replaced, and the viewing element is mounted to move on the platform.

3. A device for establishing an anatomical reference point of an intervertebral disc according to claim 1, wherein the adjusting elements comprise means for adjusting the orientation of the viewing element arranged for enabling the pivoting of the viewing element about an axis perpendicular to the longitudinal axis.

4. A device for establishing an anatomical reference point of an intervertebral disc according to claim 3, wherein the adjusting means comprise an intermediate part placed between the viewing element and the platform, the intermediate part having a convex face whereon the viewing element is mounted to move, with the intermediate part having a degree of freedom in translation along the longitudinal axis.

5. A device for establishing an anatomical reference point of an intervertebral disc according to claim 1, wherein the coupling element is mounted to slide along the viewing element.

6. A device for establishing an anatomical reference point of an intervertebral disc according to claim 1, wherein the coupling element comprises two coupling points for the respective attachment of an implantation instrument, with the coupling points being positioned on either side of the viewing element.

7. A device for establishing an anatomical reference point of an intervertebral disc according to claim 6, comprising two implantation instruments, each implantation instrument comprises a linking arm able to be mounted to be hinged on one of the coupling points of the coupling element at one of the ends thereof, with the other end being provided with a tubular portion curved according to a determined radius towards the intervertebral disc to be replaced, the curved portion is so arranged on the linking arm that the curved portion of each implantation instrument is positioned in the same plane.

8. A device for establishing an anatomical reference point of an intervertebral disc according to claim 1, wherein the device comprises first and second means for respectively blocking the platform on the first and second bone anchors and the viewing element on the platform.

9. A device for establishing an anatomical reference point of an intervertebral disc according to claim 1, wherein the platform further comprises additional coupling means enabling to attach the device on a holding equipment able to be attached on a support and provided with complementary coupling means.

10. A device for establishing an anatomical reference point of an intervertebral disc according to claim 1, wherein the connector comprises a linking bar able to link the first and second bone anchors together, the platform being mounted on the linking bar.

11. A device for establishing an anatomical reference point of an intervertebral disc according to claim 10, wherein the platform and the linking bar comprise the ball and socket link.

12. A device for establishing an anatomical reference point of an intervertebral disc according to claim 11, wherein ball and socket link comprises a spherical joint provided on one of the platform and the linking bar, the spherical joint cooperating with a recess having a matching shape provided on the other element.

13. A device for establishing an anatomical reference point of an intervertebral disc according to claim 1, wherein the instrument rotates around an axis perpendicular to the longitudinal axis and the vertical axis.

\* \* \* \* \*